United States Patent
Brassil

(10) Patent No.: US 8,986,978 B2
(45) Date of Patent: Mar. 24, 2015

(54) PERFUSION REGULATION

(75) Inventor: John Brassil, Northbrook, IL (US)

(73) Assignee: Lifeline Scientific, Inc., Des Plaines, IL (US)

( * ) Notice: Subject to any disclaimer, the term of this patent is extended or adjusted under 35 U.S.C. 154(b) by 724 days.

(21) Appl. No.: 12/449,846

(22) PCT Filed: Feb. 29, 2008

(86) PCT No.: PCT/US2008/002734
§ 371 (c)(1),
(2), (4) Date: Aug. 31, 2009

(87) PCT Pub. No.: WO2008/108996
PCT Pub. Date: Sep. 12, 2008

(65) Prior Publication Data
US 2010/0028850 A1    Feb. 4, 2010

Related U.S. Application Data

(60) Provisional application No. 60/904,190, filed on Mar. 1, 2007.

(51) Int. Cl.
*A01N 1/02*    (2006.01)

(52) U.S. Cl.
CPC .............. *A01N 1/02* (2013.01); *A01N 1/0247* (2013.01)
USPC ...................................... 435/284.1

(58) Field of Classification Search
CPC .............................. A01N 1/0247; A01N 1/02
USPC .................................. 435/284.1
See application file for complete search history.

(56) References Cited

U.S. PATENT DOCUMENTS

| | | | |
|---|---|---|---|
| 3,738,914 A | 6/1973 | Thorne et al. |
| 3,892,628 A | 7/1975 | Thorne et al. |
| 3,995,444 A | 12/1976 | Clark et al. |
| 4,629,686 A | 12/1986 | Gruenberg |
| 4,745,759 A | 5/1988 | Bauer et al. |
| 5,051,352 A | 9/1991 | Martindale et al. |
| 5,069,662 A | 12/1991 | Bodden |
| 5,141,847 A | 8/1992 | Sugimachi et al. |
| 5,157,930 A | 10/1992 | McGhee et al. |

(Continued)

FOREIGN PATENT DOCUMENTS

| | | |
|---|---|---|
| CN | 1543785 A | 11/2004 |
| JP | A-2004-513889 | 5/2004 |

OTHER PUBLICATIONS

U.S. Appl. No. 09/162,128, filed Sep. 29, 1998.
Daemen et al., "Short-term outcome of kidney transplants from non-heart-beating donors after preservation by machine perfusion," *Transpl. Int*, 1996, 9, [Suppl 1]: S76-S80.

(Continued)

*Primary Examiner* — Jonathan Hurst
(74) *Attorney, Agent, or Firm* — Oliff PLC

(57) ABSTRACT

A system and method for regulating cooperatively the pressures and flows of input vessels such as both the portal vein and hepatic artery for the liver. This invention solves problems of less-than-therapeutic portal vein flow during perfusion preservation by implementing cooperative regulation between the inputs, e.g., portal vein and hepatic artery pumping systems, on an organ preservation apparatus. It includes an algorithm that adapts to the situation wherein the portal vein has reached minimum flow and maximum pressure. The cooperative regulation algorithm senses the problem with the portal vein and solves it by adjusting the hepatic artery flow conditions.

10 Claims, 13 Drawing Sheets

(56) References Cited

U.S. PATENT DOCUMENTS

| | | |
|---|---|---|
| 5,217,860 A | 6/1993 | Fahy et al. |
| 5,285,657 A | 2/1994 | Bacchi et al. |
| 5,338,662 A | 8/1994 | Sadri |
| 5,472,876 A | 12/1995 | Fahy |
| 5,476,763 A | 12/1995 | Bacchi et al. |
| 5,494,822 A | 2/1996 | Sadri |
| 5,586,438 A | 12/1996 | Fahy |
| 6,014,864 A | 1/2000 | Owen |
| 6,046,046 A | 4/2000 | Hassanein |
| 6,209,343 B1 | 4/2001 | Owen |
| 6,492,103 B1 | 12/2002 | Taylor |
| 6,673,594 B1 | 1/2004 | Owen et al. |
| 6,977,140 B1 | 12/2005 | Owen et al. |
| 7,410,474 B1 | 8/2008 | Friend et al. |
| 8,323,954 B2 | 12/2012 | Kravitz et al. |
| 2002/0012988 A1 | 1/2002 | Brasile |
| 2004/0111104 A1 | 6/2004 | Schein et al. |
| 2004/0221719 A1 | 11/2004 | Wright et al. |
| 2004/0248281 A1 | 12/2004 | Wright et al. |
| 2005/0255442 A1 | 11/2005 | Brassil et al. |
| 2011/0183310 A1 | 7/2011 | Kravitz et al. |

OTHER PUBLICATIONS

Yland et al., "An automated and portable low-flow pulsatile perfusion system for organ preservation," *Transpl. Int*, 1996, 9: 535-540.

Sep. 13, 2012 Office Action issued in Chinese Application No. 200880014135.6 (with English translation).

May 23, 2012 Office Action issued in Canadian Application No. 2,679,827.

Jul. 23, 2008 International Search Report and Written Opinion issued in Application No. PCT/US2008/002734.

Mar. 12, 2012 Office Action issued in Chinese Application No. 200880014135.6 (with English translation).

Kitagawa, "Studies of the Control of Hepatic Circulation with Special Reference to Its Auto-Regulation and The Relationship between Hepatic Artery and Portal Vein System," Journal of the Juzen Medical Society of Kanazawa University, vol. 74, No. 2, pp. 223-231, 1966, with English-language Abstract.

Jan. 22, 2013 Notice of Reasons for Rejection issued in Japanese Application No. 2009-551745, with English-language translation.

Aug. 2, 2013 Final Rejection issued in Japanese Application No. 2009-551745, with English-language translation.

Apr. 8, 2013 Canadian Office Action issued in Canadian Application No. 2,679,827.

PERFUSION REGULATION

TECHNICAL FIELD

This disclosure is directed to methods and systems for perfusing, in a defined and controlled manner, one or more organs, tissues or the like (hereinafter "organs") to sustain, maintain or improve the viability of the organs.

BACKGROUND

Perfusion apparatus for transplantable organs are described in the scientific and patent literature. For example, U.S. Pat. No. 6,977,140, assigned to Organ Recovery Systems, Inc., which is hereby incorporated by reference herein in its entirety, describes such an apparatus. U.S. Pat. No. 6,977,140 does not, however, address certain aspects of perfusing a multi-inflow organ, such as a human liver.

Ideally organs are harvested in a manner that limits their warm ischemia time. Unfortunately, many organs, especially from non-beating heart donors, are harvested after extended warm ischemia time periods, e.g., 45 minutes or more. Machine perfusion of these organs at low temperature is preferable (Transpl Int 1996 Daemen). Further, low temperature machine perfusion of organs at low pressures is also preferable (Transpl. Int 1996 Yland). Roller or diaphragm pumps are often used to deliver perfusate at controlled pressures. Numerous control circuits and pumping configurations are used to achieve preferable perfusion conditions. See, for example, U.S. Pat. Nos. 5,338,662 and 5,494,822 to Sadri; U.S. Pat. No. 4,745,759 to Bauer et al.; U.S. Pat. Nos. 5,217,860 and 5,472,876 to Fahy et al.; U.S. Pat. No. 5,051,352 to Martindale et al.; U.S. Pat. No. 3,995,444 to Clark et al.; U.S. Pat. No. 4,629,686 to Gruenberg; U.S. Pat. Nos. 3,738,914 and 3,892,628 to Thorne et al.; U.S. Pat. Nos. 5,285,657 and 5,476,763 to Bacchi et al.; U.S. Pat. No. 5,157,930 to McGhee et al.; and U.S. Pat. No. 5,141,847 to Sugimachi et al.

Use of the above described pumps for machine perfusion of organs, however, may introduce a risk of under- or over-pressurization of the organ. High pressure perfusion, above about 60 mm Hg, for example, can wash off the vascular endothelial lining of the organ and damage organ tissue. In particular, at hypothermic temperatures, an organ does not have neurological or endocrinal connections to protect itself by dilating its vasculature under high pressure. Low pressure perfusion may provide insufficient perfusate to the organ resulting in organ failure.

This concern over precise control is particularly acute in multi-inflow organs. In the living liver, blood flows into the organ via the portal vein and the hepatic artery. The blood combines in the sinusoids of the liver, and then flows out through the hepatic vein. In vivo, the hepatic artery receives relatively higher pressure arterial blood (ca. 100 mmHg), while the portal vein receives relatively lower pressure venial blood (ca. 18 mmHg). A system of vascular tension and sphincters regulates the relative resistance of blood through the portal vein and hepatic artery to manage proper flow from each inflow port into the sinusoids despite the unequal initial pressures.

During organ perfusion preservation, a goal is to perfuse fluids through the vessels of the ex vivo liver (1) in sufficient volume, i.e., flow, to enable proper dilution of waste products and proper provision of nutrients; and (2) at sufficient pressure to maintain vessel patency while limiting maximum flow and pressure to avoid damage. In a single inflow organ like the kidney, for example, this often is achieved simply by regulating the pressure and flow into the single inflow artery within well-defined minimum and maximum pressure and flow therapeutic windows. Regulation methods for single inflow organs are well known.

Conventionally, flow regulation into a liver is treated just as in a kidney. The portal vein pressure and the hepatic artery pressure, and respectives flows, are separately and independently maintained within well-defined therapeutic windows between maximum and minimum levels, regulated to a constant level of pressure or flow, or a combination of both. Methods of separate and independent regulation of portal and hepatic pressure and flow are well known.

SUMMARY

A need exists for a method and system for perfusing an organ at a defined and/or controlled pressure that can take into account organ resistance, i.e., pressure/flow, to avoid damage to the organ and to maintain the organ's viability.

This disclosure is directed to methods and systems for cooperatively regulating pressures and flows of different input vessels of an organ, such as the portal vein and hepatic artery for a liver. Studies identified a phenomenon in isolated liver perfusion in which increasing flow through the hepatic artery is associated with a consequent decreasing flow through the portal vein under constant perfusion pressure, i.e., pressure-regulated, conditions. These studies revealed that the portal vein flow may decrease to a level that is below the minimum therapeutic window as the hepatic flow increases.

Disclosed methods and systems seek to address, among other objectives, problems of less-than-therapeutic portal vein flow during organ perfusion preservation by implementing cooperative regulation between the inputs, e.g., portal vein and hepatic artery pumping systems, on an organ perfusion preservation apparatus. These methods and systems may include a control algorithm that responds when conditions in the portal vein are detected to reach minimum flow and maximum pressure as measurable parameters. In such instances, the flow cannot be increased by increasing the pressure and the pressure cannot be reduced by decreasing the flow. These conditions may be resolved by implementing a cooperative control algorithm that is provided with a sensor input of the problem condition within the portal vein, and cooperatively adjusts hepatic artery flow conditions. For example, the control algorithm may reduce the hepatic artery flow, maintaining it within the hepatic artery therapeutic window, enabling the portal vein flow to return to within the therapeutic window.

In an organ perfusion apparatus, gross organ perfusion pressure may be provided by a pneumatically pressurized medical fluid reservoir controlled by a computer. The computer may be programmed to respond to an input from a sensor or similar device, for example, disposed in a flow path such as in an end of tubing placed in a vessel of the perfused organ. The computer may be used in combination with a stepping motor/cam valve or pinch valve to (1) enable perfusion pressure fine tuning, (2) prevent overpressurization, and/or (3) provide emergency flow cut-off in the vessel. Alternatively, the organ may be perfused directly from a computer controlled pump, such as a roller pump or a peristaltic pump, with proper pump control and/or sufficient fail-safe controllers to prevent overpressurization of the organ, especially as a result of a system malfunction. Substantially eliminating overpressurization potential may reduce the consequent potential damage to the vascular endothelial lining, and to the organ tissue in general, and mitigate the effects of flow competition and flow extinction in a lower pressure vessel.

Further embodiments of the control algorithm may accommodate error recognition and alarm response to aberrant conditions. Such conditions may include when the portal flow and the hepatic pressure are both reduced below the respective therapeutic windows, or when the portal vein or the hepatic vein is occluded.

Further embodiments may recognize that the vascular sphincters may operate in an on-off fashion and exhibit hysteresis in their on-off (or open-closed) pressure thresholds. As a consequence, sequencing of establishment of portal flow versus hepatic flow may become significant. For example, if higher pressure hepatic artery perfusion is established first, then the sphincters controlling the portal vein flow into the sinusoids may become closed and require an opening pressure above the portal vein pressure. If this happens, the portal flow downstream of that particular sphincter would cease and the tissue fed by that vessel would be properly perfused.

Embodiments may recognize the action of the sphincters and implement a control algorithm that establishes a sequence of portal vein-before-hepatic artery flow. This sequence recognizes that the organ perfusion apparatus may undergo numerous startings and stoppings of flow to accommodate bubble purging, fault recovery, drug dosing, organ adjustments and other effects. Some of these events are described in the above-enumerated patent disclosures.

An organ diagnostic apparatus may also be provided to produce diagnostic data such as an organ viability index. The organ diagnostic apparatus may include features of an organ perfusion apparatus, such as sensors and temperature controllers, as well as cassette interface features. The organ diagnostic apparatus may provide analysis of input and output fluids in a perfusion system. Typically, the organ diagnostic apparatus is a simplified perfusion apparatus providing diagnostic data in a single pass, in-line perfusion.

Disclosed embodiments may also provide an organ cassette that allows an organ to be easily and safely moved between apparatus for perfusing, storing, analyzing and/or transporting the organ. The organ cassette may be configured to provide uninterrupted sterile conditions and efficient heat transfer during transport, recovery, analysis and storage, including transition between the transporter, perfusion apparatus and/or organ diagnostic apparatus, and/or other apparatus.

Disclosed embodiments may also provide an organ transporter that allows for transportation of an organ, particularly over long distances. The organ transporter may include features of an organ perfusion apparatus, such as sensors and temperature controllers, as well as organ cassette interface features.

Disclosed embodiments of the perfusion apparatus, transporter, cassette, and organ diagnostic apparatus may be networked to permit remote management, tracking and monitoring of the location and therapeutic and diagnostic parameters of the organ being stored or transported. Information systems may be used to compile historical data of organ transport and storage, and provide cross-referencing with hospital and United Network for Organ Sharing (UNOS) data on the donor and recipient for the organ. The information systems may also provide outcome data to allow for ready research of perfusion parameters and transplant outcomes.

These and other features and advantages of the disclosed methods and systems are described in, or apparent from, the following detailed description of various exemplary embodiments.

BRIEF DESCRIPTION OF THE DRAWINGS

Various exemplary embodiments of disclosed methods and systems for a perfusion apparatus for implementing a control algorithm will be described, in detail, with reference to the following drawings wherein.

DETAILED DESCRIPTION OF PREFERRED EMBODIMENTS

Figure 1:
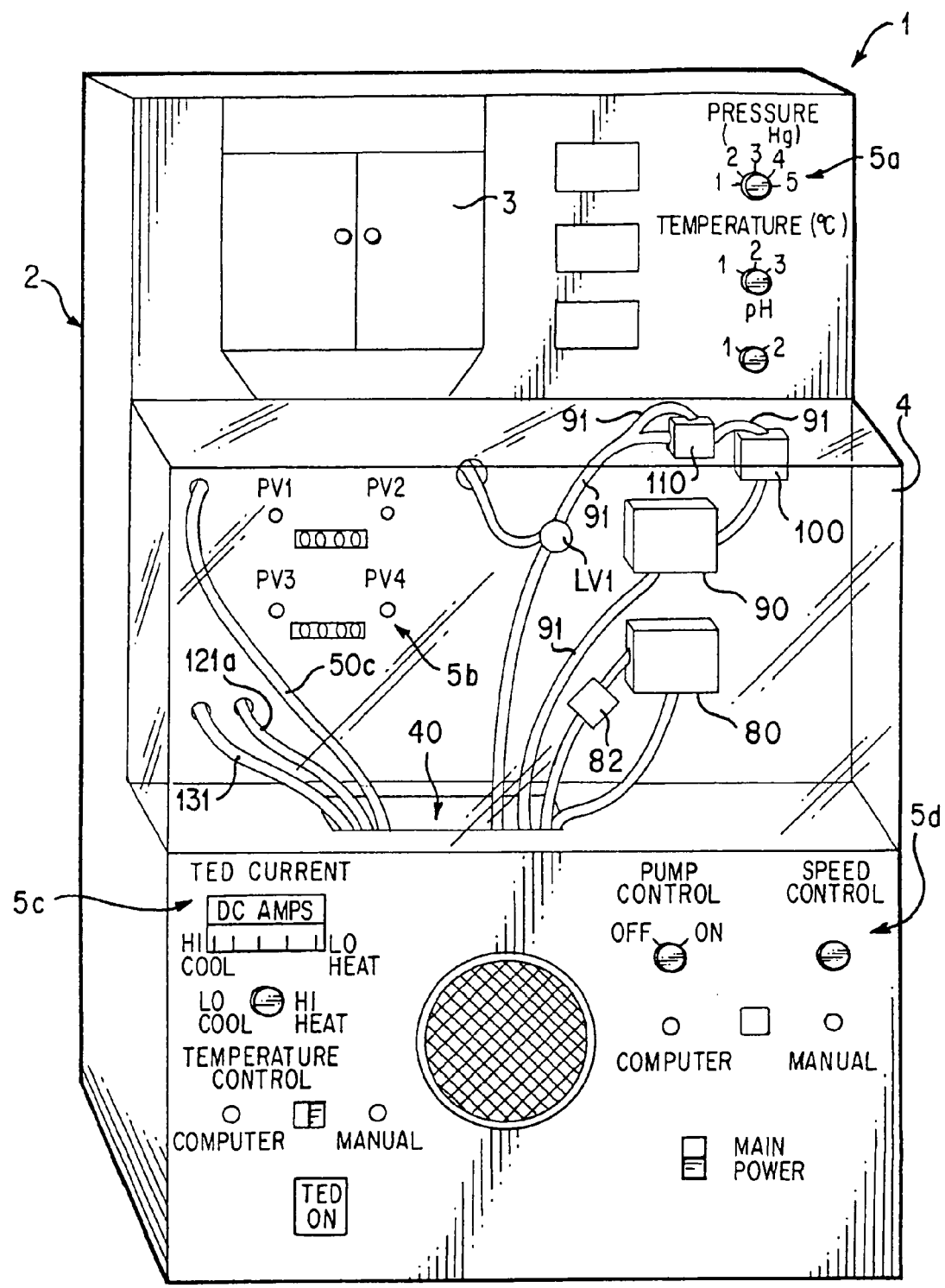
FIG. 1 illustrates an organ perfusion apparatus according to this disclosure.

For a general understanding of the features of the invention, reference is made to the drawings. In the drawings, like reference numerals have been used throughout to designate like elements.

Disclosed systems and methods are involved in transport, storage, perfusion and diagnosis of organs. However, the disclosed systems and methods may have other applications, and thus should not be construed to be limited to particular contexts of use. Various disclosed features may be particularly suitable for use in the context of, and in conjunction and/or connection with the features of the apparatus and methods disclosed in U.S. patent application Ser. No. 09/162, 128 (now abandoned), U.S. Pat. Nos. 6,977,140 and 6,673, 594, and U.S. Patent Application Publications Nos. 2004-0248281, 2004-0221719, and 2004-0111104, the disclosures of which are hereby incorporated by reference herein in their entirety.

Figure 2:
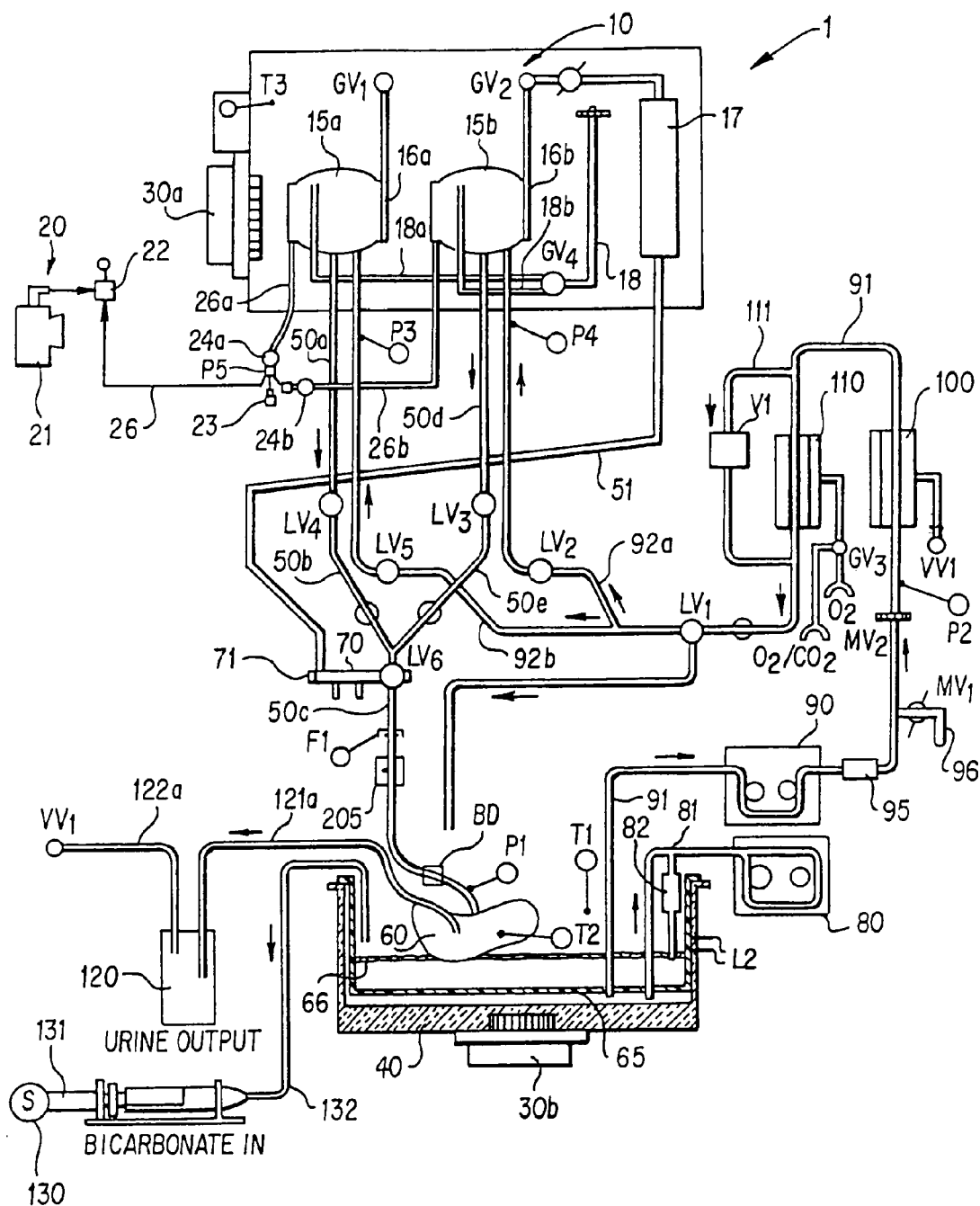
FIG. 2 is a schematic diagram of the apparatus of FIG. 1.
Figure 3:
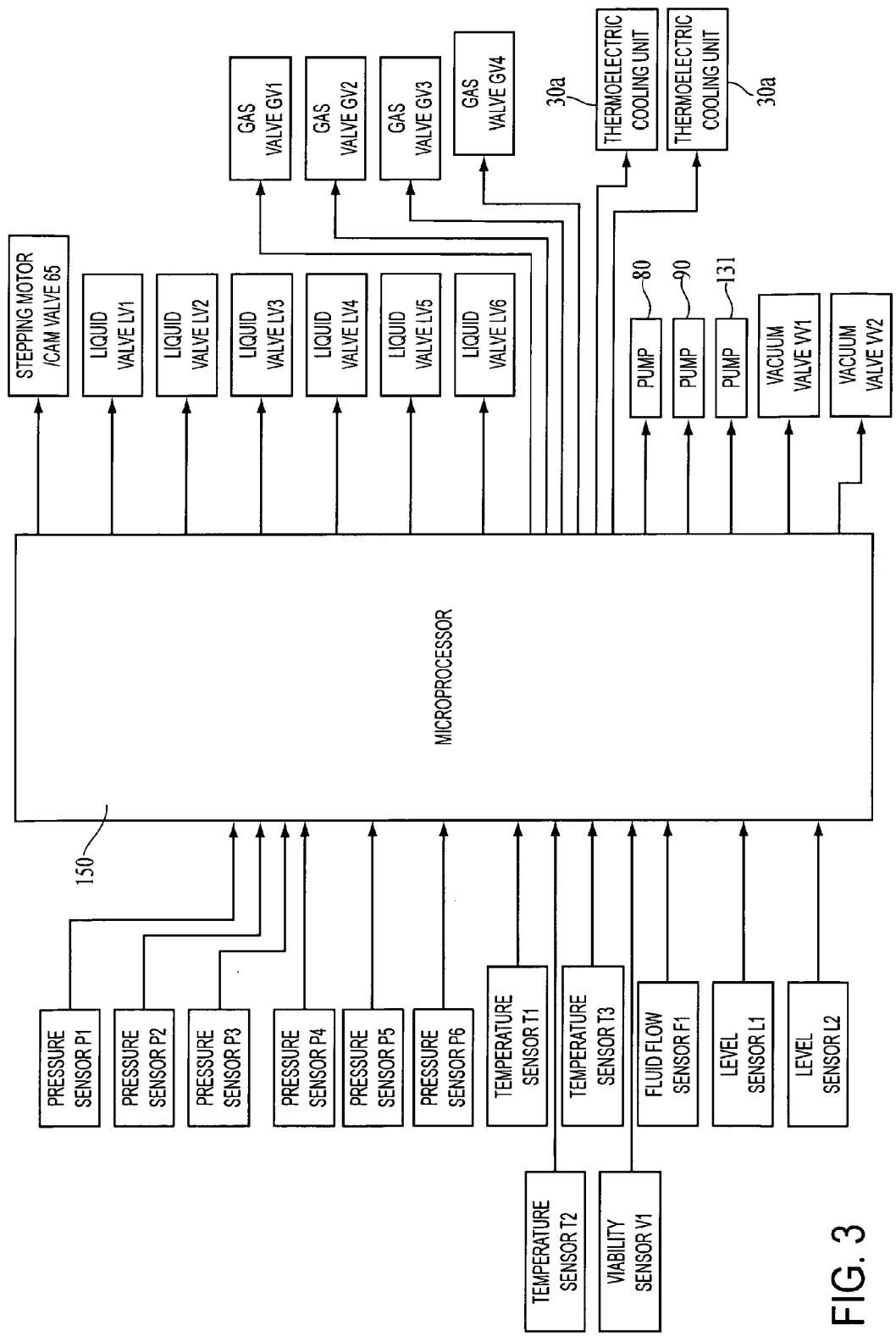
FIG. 3 is a diagram of a microprocessor controller which may be integrated with the apparatus of FIG. 2, the organ cassette of FIG. 4D, and/or the organ transporter of FIG. 9.

FIG. 1 illustrates an organ perfusion apparatus 1. FIG. 2 is a schematic illustration of the apparatus 1 of FIG. 1. The apparatus 1 may be at least partially microprocessor controlled, and pneumatically actuated. A microprocessor 150 with connections to sensors, valves, thermoelectric units and pumps of apparatus 1 is schematically depicted in FIG. 3. Microprocessor 150 and apparatus 1 may be configured to be further connected to a computer network to provide data sharing, for example, across a local area network or across the Internet.

The apparatus 1 may be capable of perfusing one or more organs simultaneously, at both normothermic and hypothermic temperatures. All medical fluid contact surfaces may be formed of, or coated with, materials compatible with the medical fluid used, more preferably non-thrombogenic materials. As shown in FIG. 1, the apparatus 1 may include a housing 2 that includes front cover 4, which may be translucent, and a reservoir access door 3. The apparatus 1 may include one or more control and display areas 5a, 5b, 5c, 5d for monitoring and controlling perfusion.

As schematically shown in FIG. 2, enclosed within the housing 2 is a reservoir 10 that may include multiple reservoir tanks such as the depicted three reservoir tanks 15a, 15b, 17. Reservoir tanks, depicted as 15a, 15b, may be standard one liter infusion bags, each with a respective pressure cuff 16a, 16b. A pressure source 20 may be provided for pressurizing the pressure cuffs 16a, 16b. The pressure source 20 may be pneumatic and may include an onboard compressor unit 21 supplying external cuff activation via gas tubes 26, 26a, 26b, as shown in FIG. 2. Disclosed embodiments, however, are not limited to use of an onboard compressor unit as any adequate pressure source can be employed. Other available pressures sources may include a compressed gas (e.g., air, $CO_2$, oxygen, nitrogen, etc.) tank (not shown). Alternatively, an internally-pressurized reservoir tank (not shown) may be used. Reservoir tanks 15a, 15b, 17 may, in embodiments, be bottles or other suitably rigid reservoirs that can supply perfusate by gravity or can be pressurized by compressed gas.

Gas valves 22 and 23 may be provided on gas tube 26 to allow for control of the pressure provided by the onboard compressor unit 21. Anti-backflow valves 24a, 24b may be provided respectively on gas tubes 26a, 26b. Pressure sensors P1, P2, P3, P4, P5, and P6 may be provided to relay detected pressure conditions to the microprocessor 150, shown in FIG. 3. Corresponding flow sensors (not shown) may also be provided. The perfusion, diagnostic and/or transporter apparatus may be provided with sensors to monitor perfusion fluid pressure and flow in the particular apparatus to detect faults in the particular apparatus, such as pressure elevated above a suitable level for maintenance of the organ. Gas valves $GV_1$ and $GV_2$ may be provided to release pressure from the cuffs 16a, 16b. One or both of gas valves $GV_1$ and $GV_2$ may be vented to the atmosphere. Gas valve $GV_4$ in communication with reservoir tanks 15a, 15b via tubing 18a, 18b may be provided to vent air from the reservoir tanks 15a, 15b through tubing 18. Tubing 18, 18a, 18b, 26, 26a and/or 26b may be configured with filters and/or check valves to prevent biological materials from entering the tubing or from proceeding along the fluid path. The check valves and/or filters may be used to prevent biological materials from leaving one organ perfusion tubeset and being transferred to the tubeset of a subsequent organ in a multiple organ perfusion configuration. The check valves and/or filters may also be used to prevent biological materials, such as bacteria and viruses, from being transferred from organ to organ in subsequent uses of the perfusion apparatus in the event that such biological materials remain in the perfusion apparatus after use. The check valves and/or filters may be provided to prevent contamination problems associated with reflux in the gas and/or vent lines. For example, the valves may be configured as anti-reflux valves to prevent reflux. The third reservoir tank 17 is preferably pressurized by pressure released from one of the pressure cuffs via gas valve $GV_2$.

The medical fluid may be a natural fluid, such as blood, or otherwise synthetic fluid, which may, for example, be a simple crystalloid solution, or may be augmented with an appropriate oxygen carrier. The oxygen carrier may, for example, be washed, stabilized red blood cells, cross-linked hemoglobin, pegolated hemoglobin or fluorocarbon based emulsions. The medical fluid may also contain antioxidants known to reduce peroxidation or free radical damage in the physiological environment and specific agents known to aid in organ protection. An oxygenated, e.g., cross-linked hemoglobin-based bicarbonate, solution may be preferred for a normothermic mode while a non-oxygenated, e.g., simple crystalloid solution preferably augmented with antioxidants, solution may be preferred for a hypothermic mode. The specific medical fluids used in both the normothermic and hypothermic modes may be designed or selected to reduce or otherwise prevent the washing away of, or damage to, the vascular endothelial lining of the organ. For a hypothermic perfusion mode, as well as for flush and/or static storage, a preferred solution is disclosed in U.S. Pat. No. 6,492,103, the disclosure of which is hereby incorporated herein by reference in its entirety. Examples of additives which may be used in perfusion solutions are also disclosed in U.S. Pat. No. 6,046,046 to Hassanein, the disclosure of which is hereby incorporated by reference herein in its entirety. Other suitable solutions and materials may be used.

The medical fluid within reservoir 10 may be brought to a predetermined temperature by a first thermoelectric unit 30a in heat transfer communication with the reservoir 10. A temperature sensor T3 may relay the temperature within the reservoir 10 to the microprocessor 150, which adjusts some in turn the thermoelectric unit 30a to maintain a desired temperature within the reservoir 10 and/or display the temperature on a control and display area such as 5a for manual adjustment. Alternatively, or in addition, particularly where the organ perfusion device is going to be transported, the medical fluid within the reservoir 10 can be cooled utilizing a cryogenic fluid heat exchanger apparatus such as that disclosed in U.S. Pat. No. 6,014,864, the disclosure of which is hereby incorporated by reference herein in its entirety.

An organ chamber 40 may be provided which supports a cassette 65, as shown in FIG. 2. The cassette 65 may be configured to hold an organ to be perfused. Otherwise the organ chamber 40 may support a plurality of cassettes 65, as shown in FIG. 5, which may be disposed one adjacent the other. Various embodiments of the cassette 65 are shown in FIGS. 4A-4D. The cassette 65 may be formed of a material that is light but durable so that the cassette 65 is highly portable. The material may also be transparent to allow visual inspection of the organ.

Figure 4A:
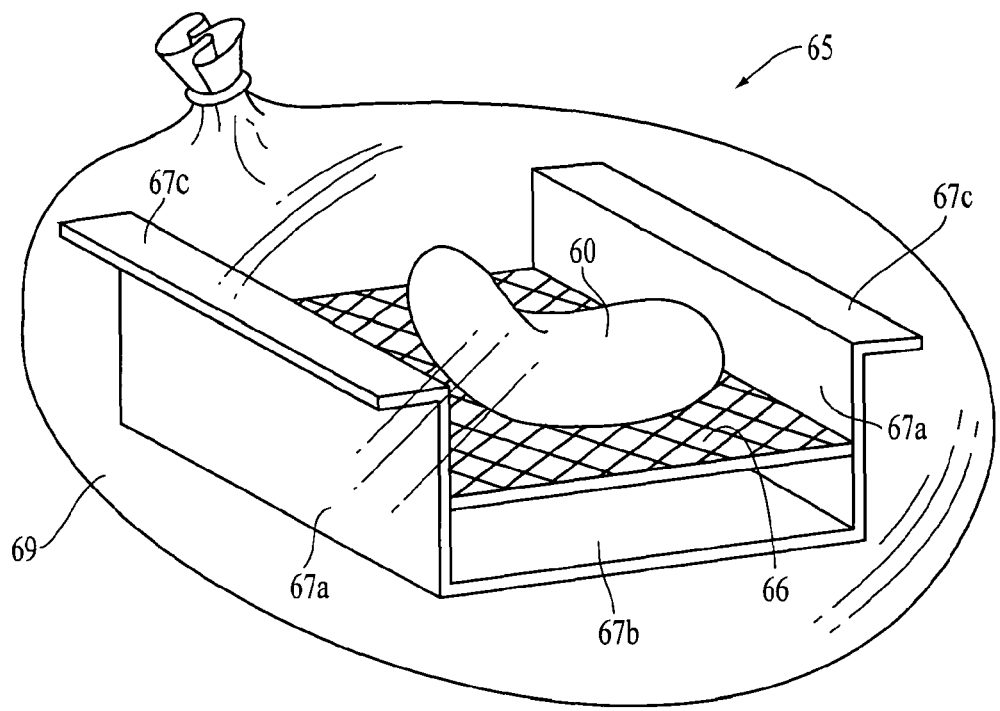
FIGS. 4A-4D are perspective views of various embodiments of an organ cassette according to the invention.
Figure 4B:
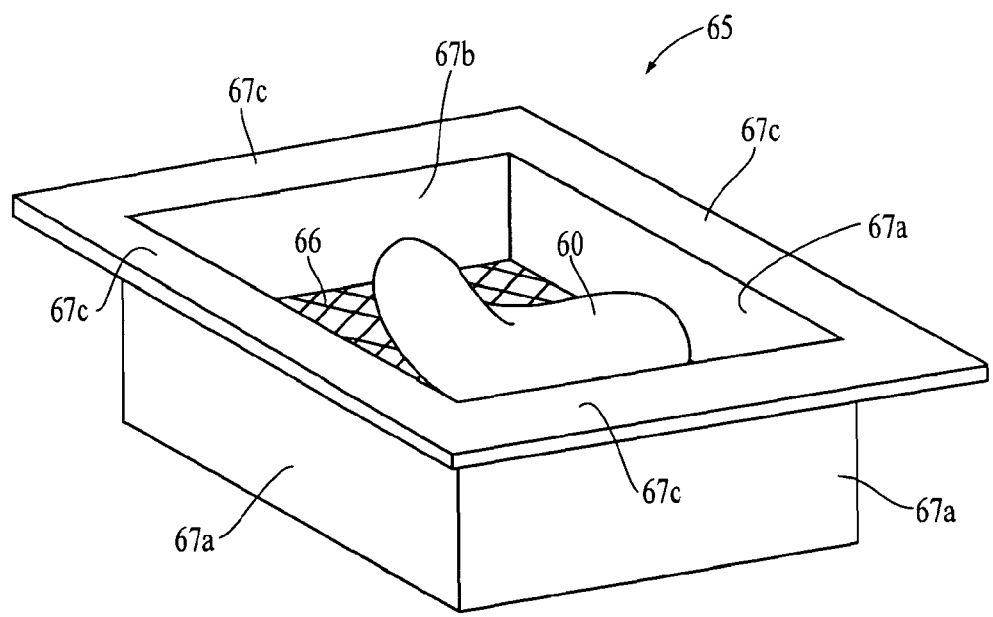
Figure 5:
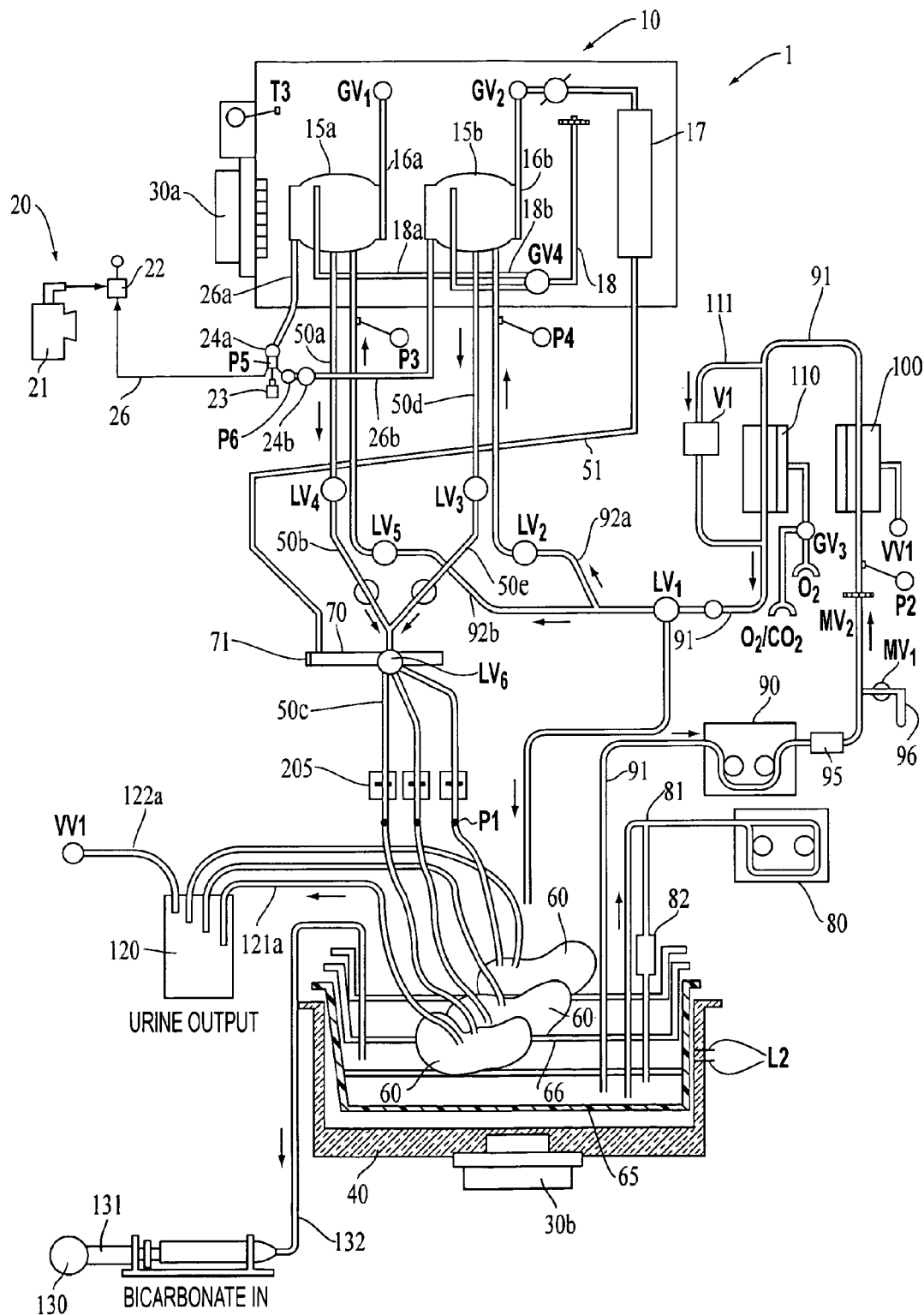
FIG. 5 is a schematic diagram of an organ perfusion apparatus configured to simultaneously perfuse multiple organs.

FIG. 4A illustrates a cassette 65 that holds an organ 60 to be perfused. The cassette 65 may include side walls 67a, a bottom wall 67b and an organ supporting surface 66. The organ supporting surface 66 may be formed of a porous, perforated or mesh material to allow fluids to pass through. The cassette 65 may also include a top 67d and may be provided with one or more openings 63 for tubing (see, for example, FIG. 4D). The openings 63 may include seals 63a, e.g., septum seals or o-ring seals and optionally be provided with plugs (not shown) to prevent contamination of the organ 60 and maintain a sterile environment. Also, cassette 65 may be provided with a closeable and/or vent 61 (see, for example, FIG. 4D). Additionally, the cassette 65 may be provided with tubing for connection to the organ 60 and/or to remove medical fluid from an organ bath, and one or more connection devices 64 for connecting the tubing to, for example, tubing 50c, 81, 82, 91 and/or 132 (see, for example, FIG. 4D) of an organ storage, transporter, perfusion and/or diagnostic apparatus.

Vent 61 may include a filter device, and provide for control and/or equalization of pressure within the cassette 65 without contamination of the contents of the cassette 65. For example, organs are frequently transported by aircraft, in which pressure changes are the norm. Even ground transportation can involve pressure changes as motor vehicles pass through tunnels, over mountains, etc. In addition, one or more lids 410 and 420 of cassette 65 can create an airtight seal with the cassette 65. This air tight seal can create a pressure difference between the inside and outside of cassette 65. It may be desirable to provide for pressure equalization of the cassette 65 under such circumstances. However, free flow of air to achieve pressure equalization might introduce contaminants into the cassette 65. Thus, a vent 61 including a filter may be provided to allow the air flow without permitting introduction of contaminants into the cassette 65.

The filter may facilitate clean air passing in both directions, while restricting dirt, dust, liquids and other contaminants from passing. The pore size of the filter can be selected to prevent bacteria from passing.

A pressure control valve (not shown) may optionally be associated with vent 61 as well. Such a valve may be configured and controlled to restrict the rate at which external pressure changes are transmitted to the inside of the cassette 65, or even to prevent pressure increases and/or decreases, as desired.

Figure 4C:
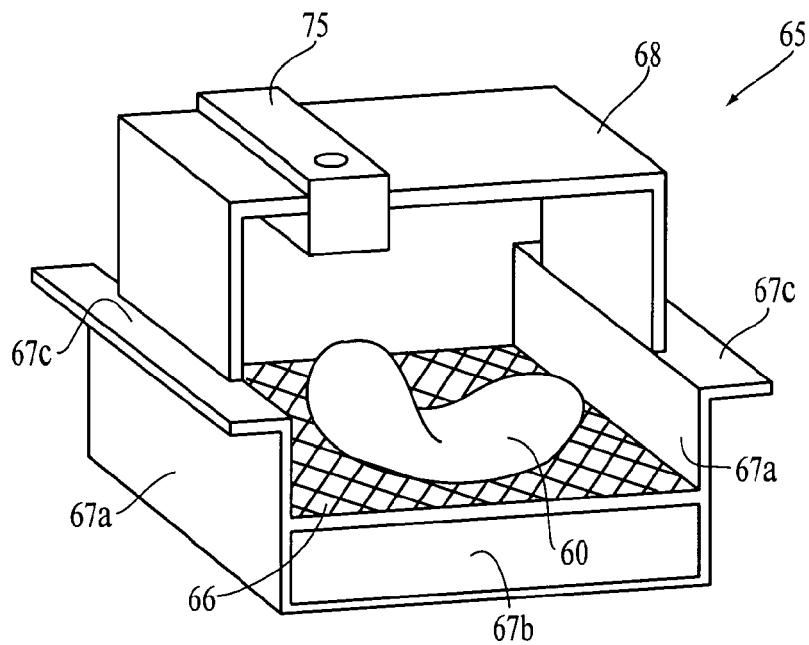
Figure 4D:
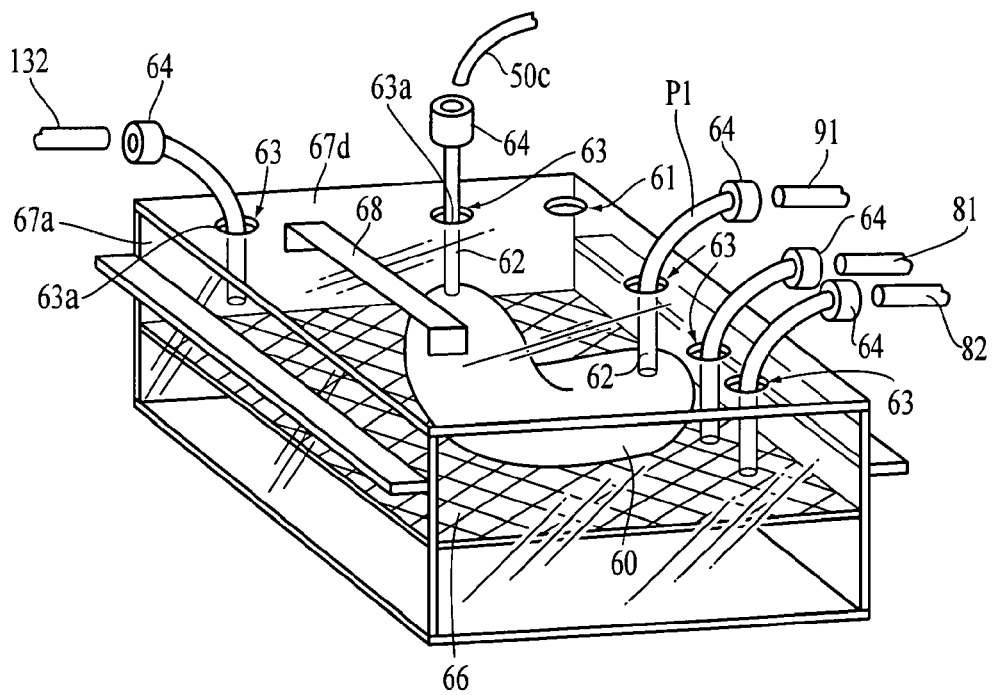

The cassette 65, and/or the organ supporting surface 66, openings 63, tubings and/or connection device 64, may be specifically tailored to the type of organ and/or size of organ to be perfused. Flanges 67c of the side support walls 67a may be used to support the cassette 65 disposed in an organ storage, transporter, perfusion and/or diagnostic apparatus. The cassette 65 may further include a handle 68 that allows the cassette 65 to be easily handled, as shown, for example, in FIGS. 4C and 4D. Each cassette 65 may also be provided with its own mechanism, e.g., stepping motor/cam valve 75 (for example, in the handle portion 68, as shown in FIG. 4C) for fine tuning the pressure of medical fluid perfused into the organ 60, as discussed in more detail below. Alternatively, or in addition, pressure may, in embodiments, be controlled by way of a microprocessor 150, as shown in FIG. 3, which may receive pressure sensor data from pressure sensor P1. Likewise, flow sensors may be controlled in a similar manner.

Figure 6A:
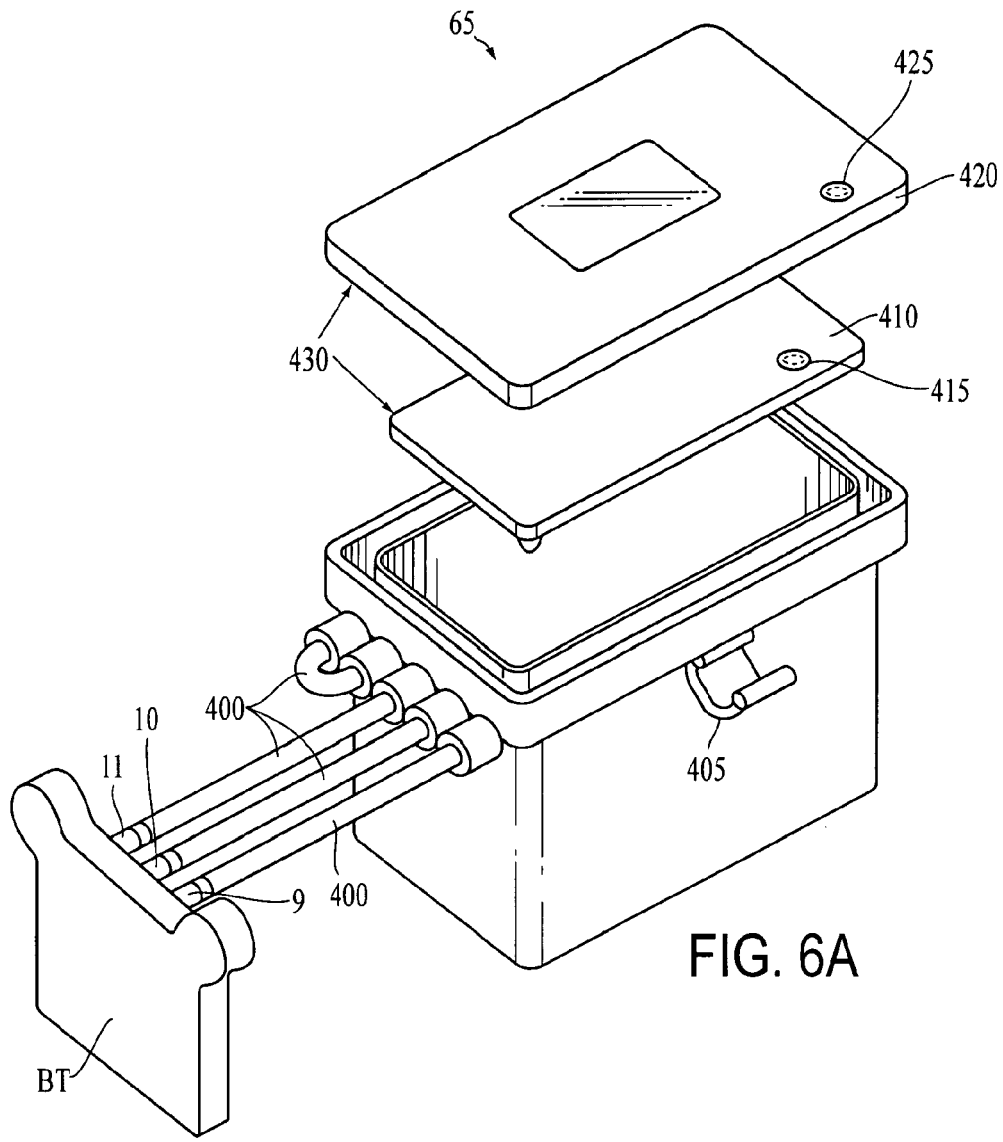
FIGS. 6A and 6B illustrate an alternate embodiment of an organ cassette according to this disclosure.
Figure 6B:
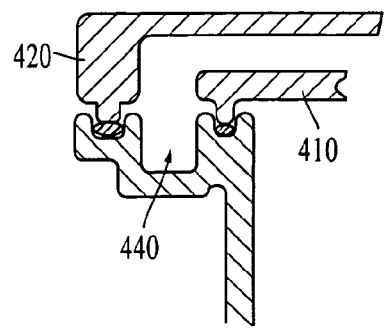

FIGS. 6A-6B illustrate an alternate embodiment of cassette 65. In FIG. 6A, cassette 65 is shown with tubeset 400. Tubeset 400 may be connected to perfusion apparatus 1, shown in other detail in FIG. 1, or to an organ transporter or an organ diagnostic apparatus. In this manner, cassette 65 may be moved between various apparatus without jeopardizing the sterility of the interior of cassette 65. Cassette 65 may be made of a sufficiently durable material that it can withstand penetration and harsh impact. Cassette 65 may be provided with one or more lids, depicted in FIG. 6A as an inner lid 410 and an outer lid 420. As shown in FIG. 6A, the tube set may be connected to a bubble trap device BT. Such a bubble trap device is described in detail in a U.S. Patent Application Publication No. US 2004-0221719, the disclosure of which is hereby incorporated by reference herein in its entirety.

The cassette 65 is a portable device. As such, the one or more lids 410, 420 can create a substantially airtight seal with the cassette 65. This air tight seal can create a pressure difference between the inside and outside of cassette 65. Pressure sensors that control perfusion of the organ may be referenced to the atmospheric pressure. In such embodiments, it is desirable that the air space around the organ in cassette 65 is maintained at atmospheric pressure. Accordingly, the cassette 65 may also include one or more devices for controlling the pressure. The devices for controlling pressure can be active or passive devices such as valves or membranes. Membranes 415, 425, for example, may be located in the inner lid 410 and outer lid 420, respectively. It should be appreciated that any number of membranes may be located in the cassette 65, including in the cassette lids 410, 420. The membranes 415, 425 are preferably hydrophobic membranes that help maintain an equal pressure between the inside and the outside of the cassette 65. The membranes 415, 425, if sufficiently flexible, may remain impermeable or substantially impermeable to collapse. Alternatively, the membranes 415, 425 may include filters that will let clean air pass in both directions. In such instances, the membranes 415, 425 should not allow dirt, dust, liquids and other contaminants to pass. The pore size in the filters of the membranes 415, 425 may be selected to prevent bacteria from passing. The presence of the membranes 415, 425, and corresponding filters, help maintain the sterility of the system.

The lids 410, 420 may be removable or may be hinged or otherwise connected to the body of cassette 65. Clasp 405, for example, may provide a mechanism to secure lids 410, 420 to the top of cassette 65. Clasp 405 may additionally be configured with a lock to provide further security and stability. A biopsy and/or venting port 430 may be included in inner lid 410, or in both inner lid 410 and outer lid 420. Port 430 may provide access to the organ 60 to allow for additional diagnosis of the organ 60 with minimal disturbance of the organ 60. Cassette 65 may also have an overflow trough 440 (shown in FIG. 6B as a channel present in the top of cassette 65). When lids 410, 420 are secured on cassette 65, overflow trough 440 may provide a region to check to determine if the inner seal is leaking. Perfusate may be poured into and out of cassette 65 and may be drained from cassette 65 through a stopcock or removable plug.

Cassette 65 and/or lids 410, 420 may be constructed of an optically transparent material to allow for viewing of the interior of cassette 65 and monitoring of the organ 60 and to allow for video images or photographs to be taken of the organ 60. A perfusion apparatus or cassette 65 may be wired and fitted with a video camera or a photographic camera, digital or otherwise, to record the progress and status of the organ 60. Captured images may be made available over a computer network such as a local area network or the Internet to provide for additional data analysis and remote monitoring. Cassette 65 may also be provided with a tag that would signal, e.g., through a bar code, magnetism, radio frequency, or other means, the location of the cassette 65, that the cassette 65 is in an apparatus 1, and/or the identity of the organ 60 to perfusion, storage, diagnostic and/or transport apparatus. Cassette 65 may be sterile packaged and/or may be packaged or sold as a single-use disposable cassette, such as in a peel-open pouch. A single-use package containing cassette 65 may also include tubeset 400 and/or tube frame 200, discussed further below.

Cassette 65 may be configured such that it may be removed from an organ perfusion apparatus and transported to another organ perfusion and/or diagnostic apparatus in a portable transporter apparatus as described herein or, for example, a conventional cooler or a portable container such as that disclosed in U.S. Pat. No. 6,209,343, or U.S. Pat. No. 5,586,438 to Fahy, the disclosures of which are hereby incorporated by reference herein in their entirety.

In various exemplary embodiments, when transported, the organ 60 may be disposed on the organ supporting surface 66 and the cassette 65 may be enclosed in a sterile bag 69, as shown, for example, in FIG. 4A. When the organ is perfused with medical fluid, effluent medical fluid collects in the bag 69 to form an organ bath. Alternatively, cassette 65 may be formed with a fluid tight lower portion in which effluent medical fluid may collect, or effluent medical fluid may collect in another compartment of an organ storage, transporter, perfusion and/or diagnostic apparatus, to form an organ bath. The bag 69 would preferably be removed prior to inserting the cassette 65 into an organ storage, transporter, perfusion and/ or diagnostic apparatus. Further, where a plurality of organs 60 are to be perfused, multiple organ compartments may be provided.

Figure 7:
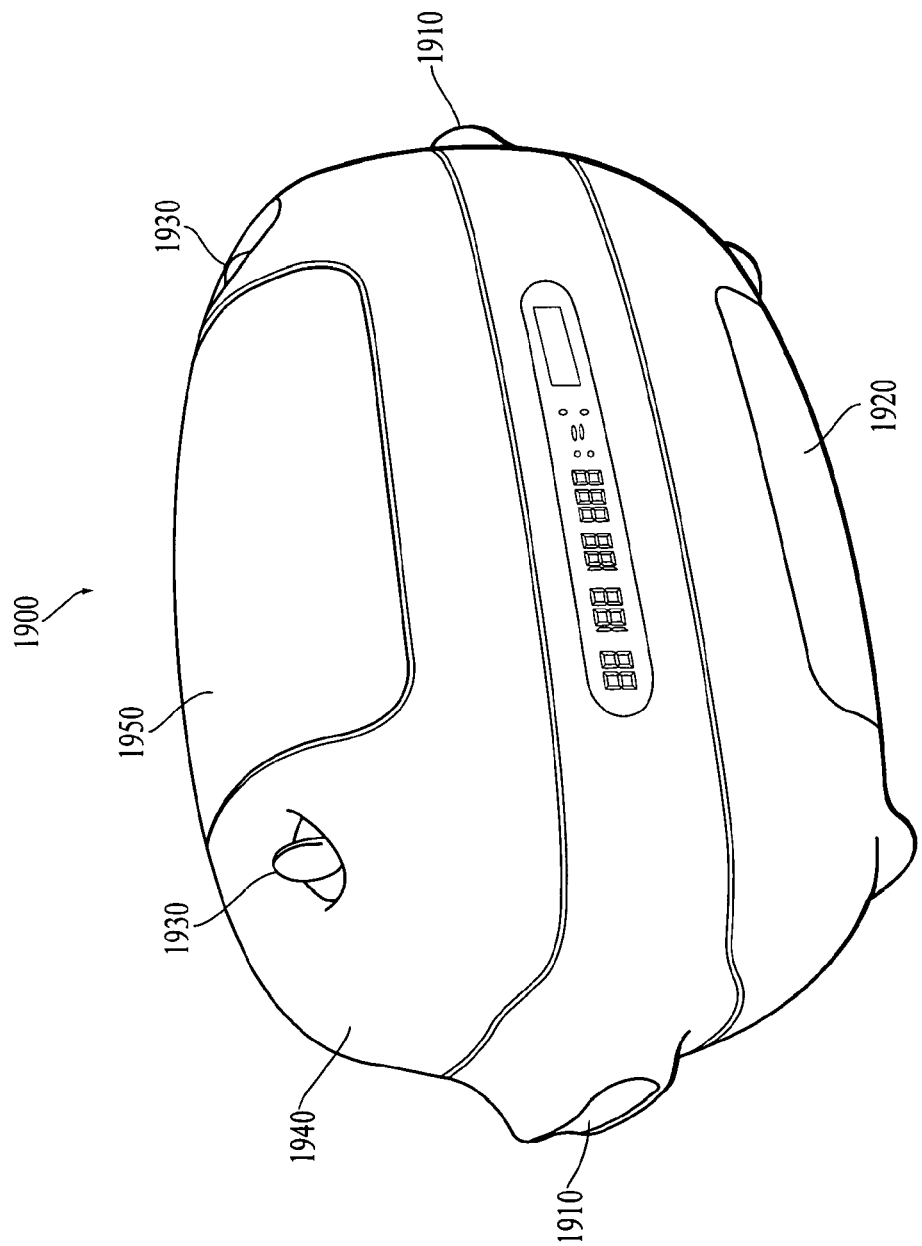
FIG. 7 shows an exterior perspective view of an organ transporter according to the present invention.

FIG. 7 shows an external view of an embodiment of a transporter 1900. The transporter 1900 of FIG. 7 has a stable base to facilitate maintaining an upright position and handles 1910 for carrying transporter 1900. Transporter 1900 may also be fitted with a shoulder strap and/or wheels to assist in carrying transporter 1900. A control panel 1920 may be provided. Control panel 1920 may display characteristics, such as, but not limited to, infusion pressure, attachment of the tube frame, power on/off, error or fault conditions, flow rate, flow resistance, infusion temperature, bath temperature, pumping time, battery charge, temperature profile (maximums and minimums), cover open or closed, history log or graph, and additional status details and messages, some or all of which may be further transmittable to a remote location for data storage and/or analysis. Flow and pressure sensors or transducers in transporter 1900 may be provided to monitor various organ characteristics including pump pressure and vascular resistance of an organ, which can be stored in computer memory to allow for analysis of, for example, vascular resistance history, as well as to detect faults in the apparatus, such as elevated pressure.

Transporter 1900 may include latches 1930 that require positive user action to open, thus avoiding the possibility that transporter 1900 inadvertently opens during transport. Latches 1930 may hold top 1940 in place on transporter 1900 in FIG. 7. Top 1940 or a portion thereof may be constructed with an optically transparent material to provide for viewing of the cassette and organ perfusion status. Transporter 1900 may be configured with a cover open detector that monitors and displays whether the cover is open or closed. Transporter 1900 may be configured with an insulating exterior of various thicknesses to allow the user to configure or select an appropriate transporter 1900 for varying extents and distances of transport. In embodiments, compartment 1950 may be provided to hold patient and organ data such as charts, testing supplies, additional batteries, hand-held computing devices and/or configured with means for displaying a UNOS label and/or identification and return shipping information.

Figure 8:
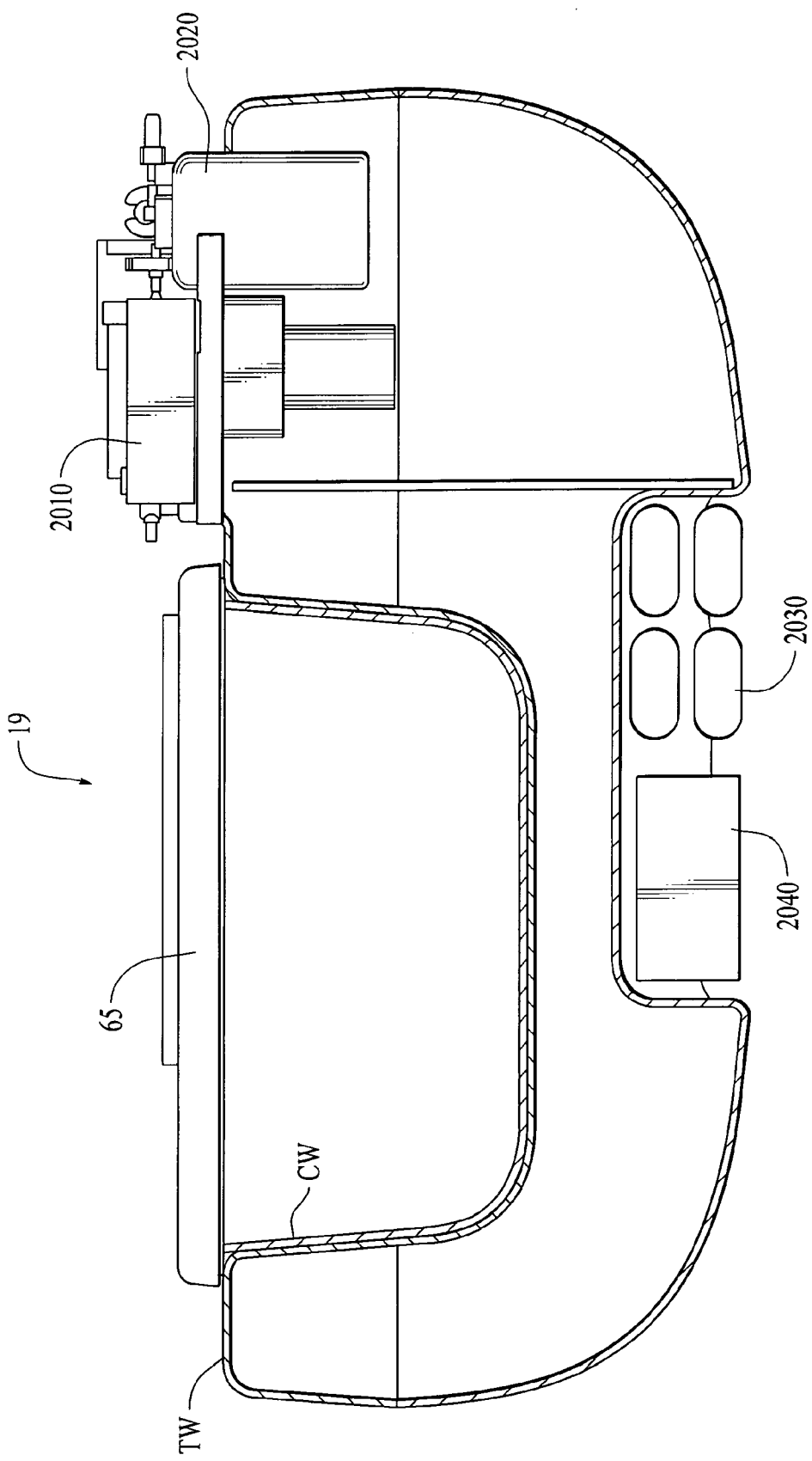
FIG. 8 is a cross-sectional view of the organ transporter of FIG. 7.

FIG. 8 is a cross-section view of a transporter 1900. Transporter 1900 may be fitted with a conformed cassette 65 and include pump 2010. Cassette 65 may preferably be placed into or taken out of transporter 1900 without disconnecting tubeset 400 from cassette 65, thus maintaining sterility of the organ. In embodiments, sensors in transporter 1900 can detect the presence of cassette 65 in transporter 1900, and, depending on the sensors, can read the organ identity from a barcode or radio frequency or other "smart" tag that may be attached, or integral, to cassette 65. This can allow for automated identification and tracking of the organ in the cassette 65, and helps to monitor and control the chain of custody. A global positioning system receiver may be added to transporter 1900 and/or cassette 65 to facilitate tracking of the organ. Transporter 1900 may be interfaceable to a computer network by hardwire connection to a local area network or by wireless communication, for example, while in transit. This interface may allow data such as perfusion parameters, vascular resistance, and organ identification, and transporter 1900 and cassette 65 location, to be tracked and displayed in real-time or captured for future analysis.

Transporter 1900 may contain a filter 2020 to remove sediment and other particulate matter from the perfusate to prevent clogging of the apparatus or the organ. Transporter 1900 may also contains batteries 2030, which may be located at the bottom of transporter 1900 or beneath pump 2010 or at any other location that provides easy access to change batteries 2030. Transporter 1900 may also provide an additional storage space 2040, for example, at the bottom of transporter 1900, for power cords, batteries and other accessories. Transporter 1900 may also include a power port for a DC hookup, e.g., to a vehicle such as an automobile or airplane, and/or for an AC hookup.

As shown in FIG. 8, the cassette wall CW of cassette 65 is preferably configured to mate with a corresponding configuration of inner transporter wall TW of the temperature 1900 to maximize contact, and facilitate heat transfer, as discussed in more detail below.

Figure 9:
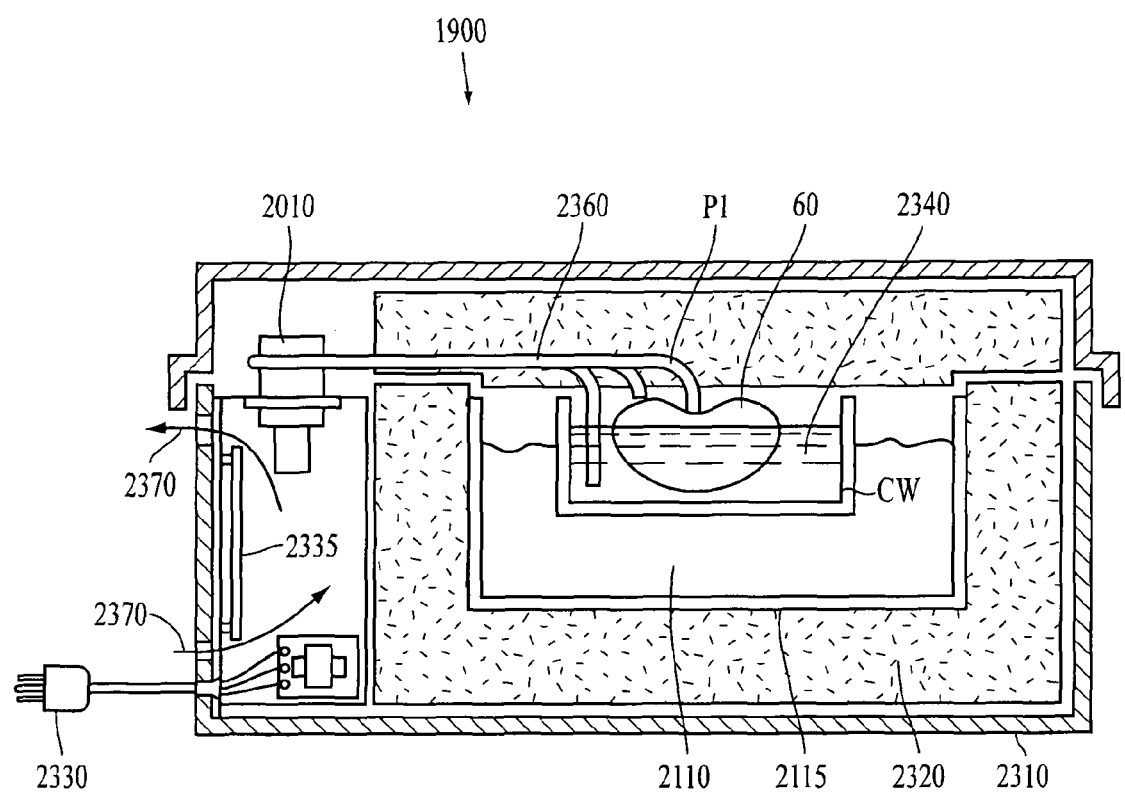
FIG. 9 is an alternative cross-sectional view of the organ transporter of FIG. 7.

FIG. 9 is an alternate cross-sectional view of transporter 1900. In FIG. 9, the transporter 1900 may have an outer enclosure 2310 which may, for example, be constructed of metal, plastic or synthetic resin that is sufficiently strong to withstand penetration and impact. Transporter 1900 may contain insulation 2320, such as a thermal insulation made of, for example, glass wool or expanded polystyrene. Insulation 2320 may be of various thicknesses. Transporter 1900 may be cooled by coolant 2110, which may be, e.g., an ice and water bath or a cryogenic material. In embodiments using cryogenic materials, the design should be such that organ freezing is prevented. Transporter 1900 may be configured to hold various amounts of coolant. An ice and water bath is preferable because it is inexpensive and generally cannot get cold enough to freeze the organ. The level of coolant 2110 may, for example, be viewed through a transparent region of transporter 1900 or be automatically detected and monitored by a sensor. Coolant 2110 may be replaced without stopping perfusion or removing cassette 65 from transporter 1900. Coolant 2110 may be maintained in a fluid-tight compartment 2115 of transporter 1900. An inner transporter wall TW as shown in FIG. 8, may be interposed between the coolant 2110 and cassette wall CW in the apparatus of FIG. 9. Compartment 2115 preferably prevents the loss of coolant 2110 in the event transporter 1900 is tipped or inverted. Heat is conducted from the walls of the cassette 65 into coolant 2110 enabling control within the desired temperature range. Coolant 2110 may provide a failsafe cooling mechanism where transporter 1900 automatically reverts to cold storage in the case of power loss or electrical or computer malfunction. Transporter 1900 may also be configured with a heater to raise the temperature of the perfusate.

An electronics module 2335 may also be provided in transporter 1900. Electronics module 2335 may be cooled by vented air convection 2370, and may further be cooled by a fan. Preferably, electronic module 2335 is positioned separate from the perfusion tubes to prevent the perfusate from wetting electronics module 2335 and to avoid adding extraneous heat from electronics module 2335 to the perfusate. Transporter 1900 may include a pump 2010 that provides pressure to perfusate tubing 2360 (e.g., of tube set 400) to deliver perfusate 2340 to organ 60. Pressure sensor P1 may be provided on perfusate tubing 2360 to relay conditions therein to the microprocessor 150, shown in FIG. 3. Transporter 1900 may be used to perfuse various organs such as a kidney, heart, liver, small intestine and lung. Transporter 1900 and cassette 65 may accommodate various amounts to perfusate 2340.

Cassette 65 and transporter 1900 may be constructed to fit or mate such that efficient heat transfer is enabled. The transporter 1900 may rely on conduction to move heat from the cassette 65 to coolant 2110 contained in compartment 2115. This movement of heat allows the transporter 1900 to maintain a desired temperature of the perfusion solution. The geometric elements of cassette 65 and transporter 1900 may be configured such that when cassette 65 is placed within transporter 1900, the contact area between cassette 65 and transporter 1900 is as large as possible and they are secured for transport.

Pump 2010, which may be a peristaltic pump, or any type of controllable pump, may be used to move fluid throughout the infusion circuit of, for example, the organ perfusion apparatus of FIG. 2, the organ cassette 65 of FIG. 6a, and/or the organ transporter 1900 of FIG. 8, and into organ 60.

It should be appreciated that the organ 60 may be any type of organ, a kidney, liver, or pancreas, for example, and the organ may be from any species, such as a human or other animal.

In a flow path for perfusate (infusion circuit), immediately preceding, or within, organ 60, may lie a pressure sensor P1, which can sense the pressure of fluid flow at the position before the fluid enters, or dispersed in, organ 60. As fluid is moved throughout the infusion circuit, organ 60 provides resistance. Pressure sensor P1 detects the pressure that the organ 60 creates by this resistance as the fluid moves through it. At a position after organ 60, there is little pressure, as the fluid typically flows out of the organ 60 freely and into an organ bath.

Figure 10:
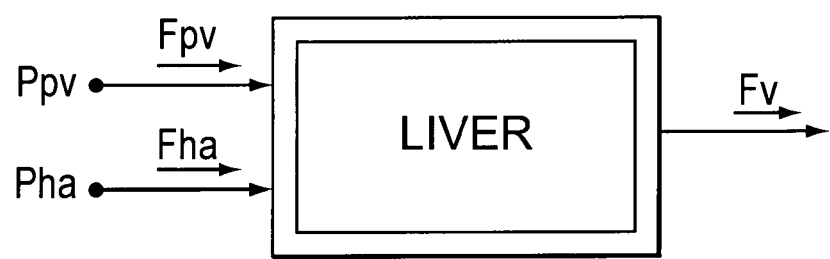
FIG. 10 is a schematic diagram of the relationship between the pressure and flow of the fluids in the hepatic artery and portal vein of a liver.

The liver is a three-terminal device where flows enter separately into the portal vein and hepatic artery and exit combined through the hepatic vein. FIG. 10 is a schematic view of the relationship between the pressure and flow of the fluid in the hepatic artery and portal vein in an exemplary embodiment of the perfusion apparatus in the liver. In FIG. 10, Fv is the flow of the fluid out of the liver in the hepatic vein. Fpv is the flow of fluid in the portal vein. Fha is the flow of the fluid in the hepatic artery. In exemplary embodiments, these values satisfy the relationship Fv=Fpv+Fha. Ppv is the pressure of fluid in the portal vein. Pha is the pressure of the fluid in the hepatic artery.

In a liver perfusion apparatus, one machine (comprising pump, valves, sensors, tubing, etc.) may supply fluid to the portal vein and a separate or related or combined machine may supply the hepatic artery (for simplicity, but without limitation, this machine or machines will be referred to herein as if they are separate "machines.")

As Pha increases, a threshold is reached at which Fpv begins to decline (f(Ppv, Pha)). After that point, if Pha continues to be increased, Fpv will decline in response. This phenomena is referred to as "flow competition." Fpv can decline to zero during flow competition, resulting in a condition of flow extinction in the portal vein. Reducing Pha will tend to reverse this effect, although there will exist an amount of hysteresis.

Figure 11:
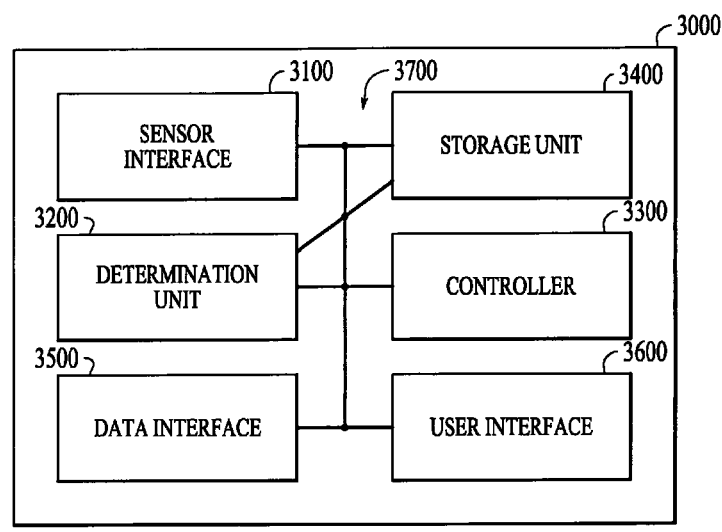
FIG. 11 illustrates a perfusion apparatus adapted to execute the disclosed control algorithm.

FIG. 11 illustrates a schematic view of an exemplary control algorithm unit 3000 for use in operating organ perfusion machines such as those described herein and is particularly adapted to provided cooperative control of the flow of fluid to a plurality of input vessels in multiple input vessel organs such as the liver. Control algorithm unit 3000 may include a sensor interface 3100, a pressure/determination unit 3200, a controller 3300 one or more storage units 3400, a data interface 3500, and a user interface 3600, all connected by a data/control buss 3700. It will be understood that the control algorithm unit 3000 may contain other units as appropriate for controlling the perfusion methods described herein. Further, control algorithm unit 3000 may be adaptable to, and may operate in conjunction with, any of the devices or apparatus envisioned by this disclosure, including, but not limited to, an organ cassette, an organ perfusion apparatus, or an organ storage device and/or an organ transporter.

The sensor interface 3100 may provide a path by which sensors (not shown) for sensing parameters of the fluid flow in the vessels of an organ 60 may transmit measurement data regarding sensed parameters to the control algorithm unit 3000. Such parameters may include, for example, the pressure and flow of the fluid flowing in one or more vessels perfusing the organ. Further, the sensor interface 3000 may be a device in the form of, for example, a microprocessor for interfacing between sensors of the apparatus in which the control algorithm unit 3000 is installed, or with which it is operating and a determination unit 3200, or may include integral sensors in the unit 3100 itself for sensing one or more parameters.

In exemplary embodiments, the sensor interface 3100 may, either directly or indirectly, sense the pressure and flow of fluids flowing in the hepatic artery and portal vein of a liver. The sensor interface 3100 may also sense the pressure and flow of fluids exiting the liver through the hepatic vein. The data may be used, for example, by the determination unit 3200 for comparison to the data prescribed by the therapeutic window or may be related to other parameters of vitality. Comparative parameter data regarding either therapeutic windows or the sensed parameters, or otherwise, may be stored in, or accessible via, for example, the one or more storage units 3400, via the data interface 3500 for connecting to an external data source, or via some user input provided at the user interface 3600, which may be configured, for example, as a graphical user interface.

The control algorithm unit 3000 may comprise a determination unit 3200. The determination unit 3200 may compare the metrics of a parameter sensed by the sensors accessible with sensor interface 3100 to the pre-set boundaries of the therapeutic window that may be available from the several data sources discussed above. The determination unit 3200 may compare the sensed values to the therapeutic window and determine whether the sensed parameter is within the therapeutic window. The determination unit 3200 may be, for example, a microprocessor.

In exemplary embodiments, the determination unit 3200 may compare the pressure and flow of fluid flowing in the hepatic artery and fluid flowing in the portal vein of the liver. It will be understood that the determination unit may make value to pre-set value comparisons, but also may be capable of higher-order valuations as needed by, for example, the complexity of the organ or the number of parameters being compared.

Based on the comparisons, the determination unit 3200 may determine whether the perfusion apparatus with which the unit 3000 is associated should be operated in an individual or cooperative capacity with regard to controlling the flow of fluid flowing in a plurality of vessels in an organ. For example, the determination unit 3200 may determine that a flow of fluid flowing in the portal vein falls outside the therapeutic window. In such an instance, the determination unit 3200 may indicate to the controller 3300 that the perfusion apparatus should be operated in a cooperative mode to manage fluid pressure and flow for the fluid flowing in both the hepatic artery and the portal vein in an effort to control the parameters in the hepatic artery in a manner to influence the flow of the fluid flowing in the portal vein back to within the therapeutic window.

The control algorithm unit 3000 may comprise a separate or integrated controller 3300 or control algorithm to execute the control functions of the unit 3000. The controller 3300 may implement an algorithm based on the determination made by the determination unit 3200. The controller 3300 may control the perfusion apparatus with which the unit 3000 is associated, or it may control individual units or devices within that apparatus. The controller 3300 may execute control to manipulate the functions of the apparatus to alter the parameters of the fluid flowing in the vessels. For example, in the liver, the controller 3300 may decrease the pressure of the fluid perfused by the apparatus perfusing the liver through the hepatic artery to cooperatively affect the flow of the fluid flowing in the portal vein. In this exemplary manner, the controller 3300 is able to manage a single or a plurality of units in an apparatus perfusing an organ, such as the liver, through a plurality of vessels by any one of, or combination of, starting, stopping, increasing or decreasing a function of the parameter of a fluid flowing through a vessel as delivered by the perfusion apparatus The unit 3000 may comprise one or more storage units 3400. The one or more storage units 3400 may operate in several capacities within the unit 3000 or outside the unit 3000 in the form of auxiliary storage media such as, for example, a computer readable storage medium with a compatible reading device. As shown in FIG. 11, in exemplary embodiments, one or more storage units 3400 may store values sensed by the sensor interface 3100 to be later provided to the determination unit 3200 or the controller 3300. The storage unit may also be capable of receiving input from the determination unit 3200 regarding, for example, determinations made but not to be applied immediately, but rather stored for a time and then sent to the controller 3300.

A control algorithm for coordinating the control of the machines within a single perfusion apparatus, such as a liver perfusion apparatus, will now be described.

The combination of flow and pressure in a vessel generally describe a therapeutic window for organ perfusion. If the flow or pressure is too high, the organ may be damaged; if the flow or pressure is too low, then the therapeutic benefits of perfusion are not realized at all, or as fully as desired. The therapeutic window is empirical, and may be established within an organ perfusion apparatus by a user or manufacturer. For example, the user may set a target value that each machine may attempt to maintain while maintaining a parameter according to a preset therapeutic value. For example, each machine may attempt to maintain a target pressure while maintaining flow above a therapeutic minimum. The organ perfusion apparatus is directed to maintaining pressure and flow within the therapeutic window.

For comparative reference, generally organs, such as kidneys, for example, are considered two-terminal devices. In a kidney, flow enters the renal artery and exits the renal vein. Flow through the kidney can be increased or decreased by increasing or decreasing the fluid pressure going into the renal artery. During perfusion, higher fluid pressure at the entrance to the renal artery delivers higher flow into the renal artery. Because the relationship between pressure and flow changes during perfusion as blood vessels tighten and loosen, an automatic controller within a kidney perfusion apparatus continually measures and adjusts pressure and flow up or down to stay within the therapeutic window. This mode of controller operation can be considered the Linear mode.

During relatively low flow conditions, such as may be encountered at the start of perfusion when the blood vessels are constricted in a liver, the flow into the portal vein and hepatic artery of a liver may be controlled independently using the Linear mode (as described for the kidney above). The pressure and flow of each vessel may be raised and lowered independently to maintain operation within appropriate therapeutic windows.

As the flow into the hepatic artery increases, a threshold is reached (which varies from liver to liver), at which further increase in hepatic artery flow may result in reduction of portal vein flow. This is flow competition. Flow competition may increase to a degree that it drives the parameter for the fluid flowing in the portal vein below the therapeutic minimum even though the portal vein pressure has reached the therapeutic maximum. At this point, further control of the portal vein within the therapeutic window cannot be maintained by adjusting the portal vein machine alone. A perfusion apparatus including the systems and methods according to this disclosure may detect such conditions and the deformentation may be made that a controller should direct the perfusion apparatus to a Cooperative mode of operation, with a goal of coordinated maintenance of both hepatic artery and portal vein pressure and flow within appropriate therapeutic windows.

During Cooperative mode operation, the controller 3300 may control the hepatic artery flow and initially reduce this flow until the portal vein flow is detected to increase back into the therapeutic window. Once both sets of pressure and flow conditions are reestablished within the therapeutic window, then revised parameters may be set by the controller 3300, which are within the therapeutic window at a sufficient value for each parameter to attempt to maintain stable perfusion in the apparatus and organ. With new parameters established, the controller 3300 may return to operating in the Linear mode, and new parameter settings may be, for example, stored in one or more storage units 3400. Furthermore, the user may be notified regarding the establishment of Cooperative mode operation and may display the new parameter settings.

In conditions where flow competition is detected, the competition can be so sever that it arrests flow in, for example, the portal vein and reduces it to zero. In such instances, the controller 3300 may operate to momentarily interrupt flow completely in the hepatic artery allowing portal vein flow to be reestablished, and, once portal vein flow is detected, to restart either Linear mode or Cooperative mode operation may be continued, where hepatic artery flow is restarted, preferentially after starting the portal vein flow under most circumstances (for example after bubble purge or fault recovery or user-directed flow start-up).

It should be recognized that leaks in a fluid circuit, occluded vessels, improperly cannulated vessels, and impact forces to the apparatus may change flow and pressure to an extent to be outside the therapeutic window. These fault conditions generally cause extreme transients outside the therapeutic window such that the fault conditions may be differentiated from flow competition. The controller 3300 may make this differentiation to determine whether to implement Cooperative mode, including recovery from portal vein extinction, or error handling, and make corrections appropriately.

Figure 12:
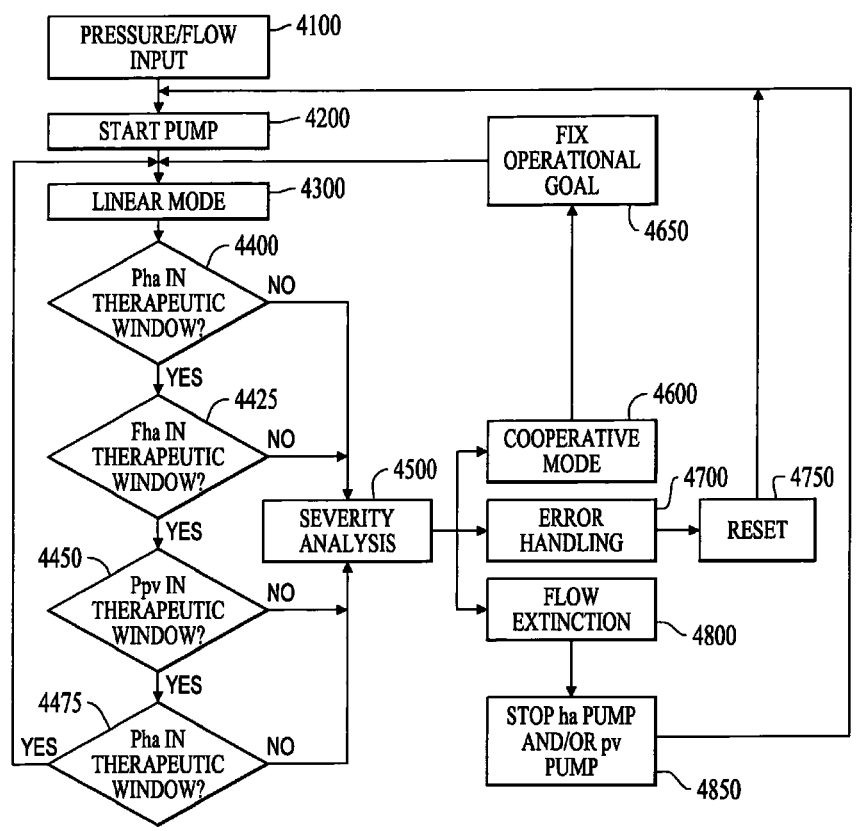
FIG. 12 is a flow chart of a method for executing the disclosed control algorithm.

With reference to FIG. 12, the following example control algorithm is provided.

In step 4100, pressure and flow of a therapeutic window are established with user settings, in apparatus pre-sets, as stored parameters, and/or combinations thereof. A user or computer sets a desired systolic pressure and/or flow, which is the pressure and flow of the fluid supply before entering the organ at pressure sensor P1, as discussed above. A peristaltic pump, for example, or any other type of controllable pump, may begin operation at step 4100.

In step 4200, the perfusion apparatus is started and operation is begun. The perfusion process is started, for example, by user pressing an INFUSE button. In step 4300, infusion of portal vein and hepatic artery flow is operated by the perfusion apparatus in an initial, likely, Linear mode. In exemplary embodiments, it is preferable to sequence a portal vein supply machine or pump to start before the hepatic artery supply machine or pump to reduce the risk of flow extinction due to flow competition at start-up.

In steps 4400, 4425, 4450 and 4475, pressure sensor P1, and the corresponding flow sensor, are queried to determine whether the pressure and flow of the fluid flowing in the hepatic artery and portal vein are within the respective therapeutic windows. If the portal vein or hepatic artery pressure or flow cannot be maintained within the respective therapeutic window, the pressure and flow environments are analyzed in step 4500 to identify the severity of causal conditions to determine whether the perfusion apparatus will go to, for example, Cooperative mode (step 4600), Error handling mode (step 4700), or Flow extinction recovery mode (step 4800).

In step 4600, the perfusion apparatus goes to Cooperative mode. In Cooperative mode, a controller may reduce hepatic artery flow until portal vein flow returns to within the therapeutic window. Then, in step 4650, the controller establishes a new hepatic artery goal pressure that is well within the therapeutic window for all parameters. After the perfusion apparatus stabilizes within the parameter(s) in the therapeutic window, the controller may cause the apparatus to return operation, in perfusion step 4300, to a Linear mode.

In step 4700, the controller may drive the perfusion apparatus to an Error handling mode. In the Error handling mode, the controller may determine if conditions suggest a fault condition such as, for example, occlusion, leak, over-pressure, or under-pressure, and then activates an alarm, coincident with implementing a stored or otherwise directed error handling and/or recovery algorithms. Based on the detected error, the controller may appropriately reset the perfusion apparatus, such as by a user, or automatically, in step 4750 and the direct the control method to return to step 4200 to restart.

In step 4800, the controller may detect actual or impending conditions of zero flow in the portal vein and drive the perfusion apparatus according to a Flow extinction mode. In an exemplary Flow extinction mode, the controller stops the hepatic artery supply machine, or both machines, in step 4850. Then, the controller operates to start portal vein flow to a set level within the therapeutic window in step 4200. After starting portal vein flow, the controller restarts hepatic artery flow. The controller then returns the perfusion apparatus to either Linear mode (step 4200) or, ultimately, Cooperative mode (step 4600) depending on the conditions of the pressure and flow environment relative to the therapeutic window.

All patents, patent applications, scientific articles and other sources and references cited herein are explicitly incorporated by reference herein for the full extent of their teachings as if set forth in their entirety explicitly in this application.

It should be understood that the foregoing disclosure emphasizes certain specific embodiments of the invention and that modifications or alternatives equivalent thereto are within the spirit and scope of the invention.

What is claimed is:

1. An apparatus for controlling at least one pump for delivering a fluid to at least one organ through a plurality of vessels for maintaining the viability of the at least one organ, comprising:
   a pump for supplying a fluid to a first vessel of an organ and to a second vessel of an organ; and
   a control algorithm unit provided with a control algorithm to execute the control functions of the unit, the control algorithm providing cooperative control of a flow of fluid to the plurality of vessels, the control algorithm unit also including:
   a sensor interface for measuring a first parameter of the fluid flowing in the first vessel and a second parameter of the fluid flowing in the second vessel,
   a controller configured to receive a measurement of at least one of the first parameter and the second parameter, the controller configured to implement the control algorithm to directly control the second parameter of the fluid flowing in the second vessel to influence the first parameter of the fluid flowing in the first vessel,
   a determination unit configured to determine that the first parameter of the fluid flowing in the first vessel falls outside of a predetermined range for the first parameter,
   wherein based upon a determination that the first parameter of the fluid flowing in the first vessel falls outside the predetermined range the controller directly control the second parameter of the fluid flowing in the second vessel to cooperatively returns the first parameter to within the predetermined range,
   a data interface, and
   a user interface, all connected by a data/control buss.

2. The apparatus of claim 1, wherein the controller directly controls the first parameter of the fluid flowing in the first vessel independently when the first parameter of the fluid in the first vessel is within the predetermined range for the first parameter.

3. The apparatus of claim 2, wherein the controller sets operational goals for the first and second parameters within predetermined ranges.

4. The apparatus of claim 3, wherein the controller resets the operational goals when the parameter of the fluid flowing in the first vessel is returned to within the predetermined range.

5. The apparatus of claim 1, further comprising:
   a storage unit for storing the predetermined range,
   wherein the predetermined range is at least one of received from a user via a user interface, recovered from a storage unit or preset in the apparatus.

6. The apparatus of claim 5,
   wherein the user interface receives the predetermined range input by the user for storing in the storage unit.

7. The apparatus of claim 1, wherein
   the determination unit is capable of detecting that the fluid has stopped flowing in the first vessel, and
   directly controlling the second parameter of the fluid flowing in the second vessel comprises stopping the flow of the fluid in the second vessel to enable restarting flow of the fluid in the first vessel.

8. The apparatus of claim 7, wherein
   the controller directly controls the fluid in the first vessel to restart flow,
   the determination unit detects flow of the fluid in the first vessel, and
   directly controlling the second parameter of the fluid flowing in the second vessel comprises restarting the flow of the fluid in the second vessel.

9. The apparatus of claim 8, wherein fluid flow is restarted in the second vessel only after flow is detected in the first vessel.

10. The apparatus of claim 1, wherein at least one of the first parameter and the second parameter is at least one of a pressure of the fluid or a flow of the fluid flowing in the respective vessel.

* * * * *